(12) United States Patent
Xue et al.

(10) Patent No.: US 8,693,747 B2
(45) Date of Patent: Apr. 8, 2014

(54) RADIOLOGICAL IMAGE NOISE REDUCTION SYSTEM AND METHOD

(75) Inventors: Ping Xue, Pewaukee, WI (US); Shijia Zhang, Beijing (CN); Fengchao Zhang, Beijing (CN); John Robert Lamberty, Oconomowoc, WI (US); Richard Gordon Cronce, New Berlin, WI (US); James Zhengshe Liu, Glenview, IL (US); Paul Richard Granfors, Berkeley, CA (US); German Guillermo Vera, Menomonee Falls, WI (US)

(73) Assignee: General Electric Company, Schenectady, NY (US)

( * ) Notice: Subject to any disclaimer, the term of this patent is extended or adjusted under 35 U.S.C. 154(b) by 468 days.

(21) Appl. No.: 13/098,275

(22) Filed: Apr. 29, 2011

(65) Prior Publication Data

US 2012/0275569 A1 Nov. 1, 2012

(51) Int. Cl.
*G06K 9/00* (2006.01)
*H01L 27/146* (2006.01)

(52) U.S. Cl.
USPC ............... 382/128; 382/275; 250/370.09

(58) Field of Classification Search
USPC ......... 382/100, 103, 106–107, 128–134, 162, 382/168, 173, 181, 199, 232, 254–260, 266, 382/274, 275–276, 305, 312; 378/21, 378/98.11, 62; 250/370.09, 515.1
See application file for complete search history.

(56) References Cited

U.S. PATENT DOCUMENTS

| | | | |
|---|---|---|---|
| 7,091,491 B2 * | 8/2006 | Kautzer et al. | 250/370.09 |
| 7,142,633 B2 * | 11/2006 | Eberhard et al. | 378/62 |
| 7,408,168 B1 * | 8/2008 | Aufrichtig et al. | 250/370.09 |
| 7,649,979 B2 * | 1/2010 | Liu et al. | 378/98.11 |
| 7,687,790 B2 * | 3/2010 | Utschig et al. | 250/515.1 |

* cited by examiner

*Primary Examiner* — Seyed Azarian
(74) *Attorney, Agent, or Firm* — Fletcher Yoder, P.C.

(57) ABSTRACT

A method for controlling a X-ray radiography system includes acquiring data from a digital X-ray detector, characterizing electromagnetic interference based upon the acquired data, selecting an electromagnetic interference compensation algorithm based upon the characterized electromagnetic interference, acquiring X-ray imaging data via the digital X-ray detector based upon the selected electromagnetic interference compensation algorithm, and processing the X-ray imaging data to produce image data capable of reconstruction in a user viewable form.

23 Claims, 4 Drawing Sheets

RADIOLOGICAL IMAGE NOISE REDUCTION SYSTEM AND METHOD

BACKGROUND OF THE INVENTION

The subject matter disclosed herein relates to digital X-ray imaging systems, and particularly to techniques for correcting effects of electromagnetic interference (EMI) in image data acquired with such systems.

A number of radiological imaging systems of various designs are known and are presently in use. Such systems generally are based upon generation of X-rays that are directed toward a subject of interest. The X-rays traverse the subject and impact a film or a digital detector. Increasingly, such X-ray systems use digital circuitry for detecting the X-rays, which are attenuated, scattered or absorbed by the intervening structures of the subject. In medical diagnostic contexts, for example, such systems may be used to visualize internal tissues and diagnose patient ailments. In other contexts, parts, baggage, parcels, and other subjects may be imaged to assess their contents and for other purposes.

Basic X-ray systems may be designed for generating projection images only. Such projection images may be presented as a well-known reverse image, although the image data itself is subject to various presentations. In addition to projection X-ray systems, the art now offers fluoroscopy systems, computed tomography systems, and tomosynthesis systems that are based on similar X-ray radiation generation and detection. In computed tomography and tomosynthesis systems, for example, images are computed as slices through the subject based upon various reconstruction techniques applied to multiple collected images. Fluoroscopy systems are used to obtain real-time moving images of the subject.

Various artifacts may be present in radiological system data collected in any one of the foregoing types of systems. Certain types of artifacts are well known and can be handled, eliminated or corrected in various known ways. However, there are still artifacts that cannot be easily corrected or avoided, at least by known techniques. For example, X-ray systems with digital detectors suffer from artifacts due to the presence of electromagnetic interference (EMI). Sources of EMI may include, for example, various electrical and electronic components that may be used in the vicinity of the X-ray imaging systems, such as radio frequency ablators, magnetic catheter navigations systems, and so forth, to mention only a few. Depending upon the phase, frequency and amplitude of such EMI, artifacts in reconstructed images may generally take the form of darker and lighter parallel rows superimposed on the basic image. Such artifacts are not only distracting, but may impair effective use of the images, such as for diagnosis in a medical context. In particular, such artifacts may make small or more detailed features that would otherwise be visible in the images, difficult to detect and discern. They may also interfere with the effective use of computer assisted techniques, such as computer assisted detection and diagnostic algorithms, segmentation algorithms, and so forth that are becoming increasingly prevalent in medical diagnostic, and part and baggage inspection contexts.

There is a need, therefore, for improved approaches to the elimination of artifacts and noise in radiological image data. There is a particular need for a technique that can address EMI-originating noise in X-ray images.

BRIEF DESCRIPTION OF THE INVENTION

In accordance with one aspect of the present disclosure, a method for controlling a X-ray radiography system includes acquiring data from a digital X-ray detector, characterizing electromagnetic interference based upon the acquired data, selecting an electromagnetic interference compensation algorithm based upon the characterized electromagnetic interference, acquiring X-ray imaging data via the digital X-ray detector based upon the selected electromagnetic interference compensation algorithm, and processing the X-ray imaging data to produce image data capable of reconstruction in a user viewable form.

In accordance with another aspect, an imaging system includes an X-ray source, a digital X-ray detector, and control circuitry. The control circuitry is configured to acquire data via the digital X-ray detector including X-ray image data and data resulting from electromagnetic interference, characterize the electromagnetic interference based upon the acquired data, select an electromagnetic interference compensation algorithm based upon the characterized electromagnetic interference, and acquire X-ray imaging data via the digital X-ray detector based upon the selected electromagnetic interference compensation algorithm. The imaging system also includes processing circuitry configured to process the X-ray imaging data to produce image data capable of reconstruction in a user viewable form.

In accordance with a further aspect, an article of manufacture includes a computer-readable storage medium having executable application instructions stored thereon. The application instructions include instructions adapted to receive first data from a digital image detector, instructions adapted to characterize electromagnetic interference based upon the received data, instructions adapted to select an electromagnetic interference compensation algorithm based upon the characterized electromagnetic interference, instructions adapted to acquire second data from the digital image detector based upon the selected electromagnetic interference compensation algorithm, and instructions adapted to process the second data to produce image data capable of reconstruction in a user viewable form.

In accordance with another aspect, a method for dynamically selecting digital X-ray detector integration time includes determining a period of an electromagnetic interference signal generated by a source external to the digital X-ray detector and adjusting an integration time of the digital X-ray detector based on the period of the electromagnetic interference signal. Adjusting includes setting the integration time as close as possible to an integer multiple of the period of the electromagnetic interference signal.

In accordance with a further aspect, a method for dynamically selecting digital X-ray detector scan line order includes determining a plurality of values of an electromagnetic interference signal generated by a source external to the digital X-ray detector using a first scan line order and sorting the plurality of values of the electromagnetic interference signal to obtain a second scan line order. The visibility of the electromagnetic interference signal is reduced in a digital X-ray image obtained using the second scan line order.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION OF THE INVENTION

Figure 1:
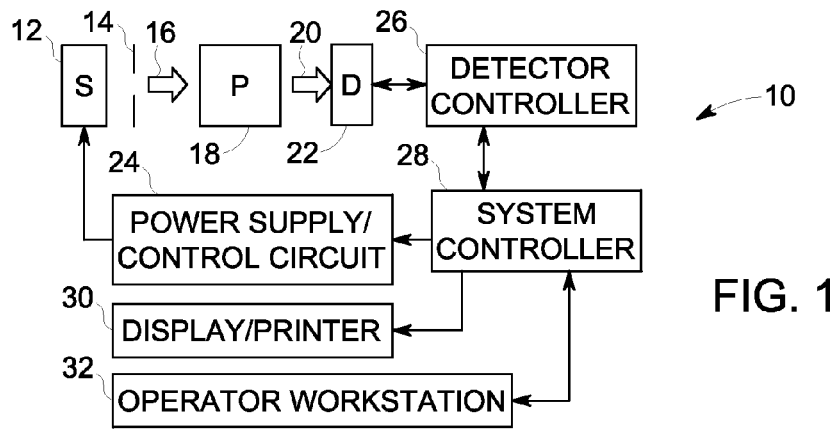
FIG. 1 is a diagrammatical overview of an exemplary digital X-ray imaging system in which the present technique may be utilized.

FIG. 1 illustrates diagrammatically an imaging system 10 for acquiring and processing discrete pixel image data. In the illustrated embodiment, system 10 is a digital X-ray system designed both to acquire original image data and to process the image data for display in accordance with the present technique. In the embodiment illustrated in FIG. 1, imaging system 10 includes a source of X-ray radiation 12 positioned adjacent to a collimator 14. Collimator 14 permits a stream of radiation 16 to pass into a region in which a subject, such as a human patient 18 is positioned. A portion of the radiation 20 passes through or around the subject and impacts a digital X-ray detector, represented generally at reference numeral 22. As described more fully below, detector 22 converts the X-ray photons received on its surface to lower energy photons, and subsequently to electric signals, which are acquired and processed to reconstruct an image of the features within the subject.

Source 12 is controlled by a power supply/control circuit 24, which furnishes both power and control signals for examination sequences. Moreover, detector 22 is coupled to a detector controller 26, which commands acquisition of the signals generated in the detector 22. Detector controller 26 may also execute various signal processing and filtration functions, such as for initial adjustment of dynamic ranges, interleaving of digital image data, and so forth. Both power supply/control circuit 24 and detector controller 26 are responsive to signals from a system controller 28. In general, system controller 28 commands operation of the imaging system 10 to execute examination protocols and to process acquired image data. In the present context, system controller 28 also includes signal processing circuitry, typically based upon a general purpose or application-specific digital computer, associated memory circuitry for storing programs and routines executed by the computer, as well as configuration parameters and image data, interface circuits, and so forth.

In the embodiment illustrated in FIG. 1, system controller 28 is linked to at least one output device, such as a display or printer as indicated at reference numeral 30. The output device may include standard or special purpose computer monitors and associated processing circuitry. One or more operator workstations 32 may be further linked in the system for outputting system parameters, requesting examinations, viewing images, and so forth. In general, displays, printers, workstations, and similar devices supplied within the system 10 may be local to the data acquisition components, or may be remote from these components, such as elsewhere within an institution or hospital, or in an entirely different location, linked to the image acquisition system via one or more configurable networks, such as the Internet, virtual private networks, and so forth.

In accordance with the present techniques, the data acquired by system 10 may be perturbed by various sources of EMI (not shown) depending upon the context in which the system is used, and the devices that may surround the system or be used in conjunction with it. Interference of various frequencies and amplitudes, some of which may be in phase and out of phase with the acquired data, may effectively be superimposed on the acquired data as it is collected. The system 10 allows for characterization and correction of such interference and thus reduction of artifacts that would otherwise be present in the image data and visible in reconstructed images based upon the data. The system 10 may use one or more of several methods depending on the characteristics of the EMI. For example, some methods may be more appropriate with certain types of EMI than other methods. Thus, the system 10 may analyze the EMI to determine which of the one or more methods to be applied to the image data. The characterization and correction itself may be carried out in any of the foregoing circuitry, including the detector circuitry, the detector controller 26, or the system controller 28. Moreover, where desired, the interference may be characterized and corrected in a post-processing step that may be partially or entirely remote from the imaging system 10 itself.

Figure 2:
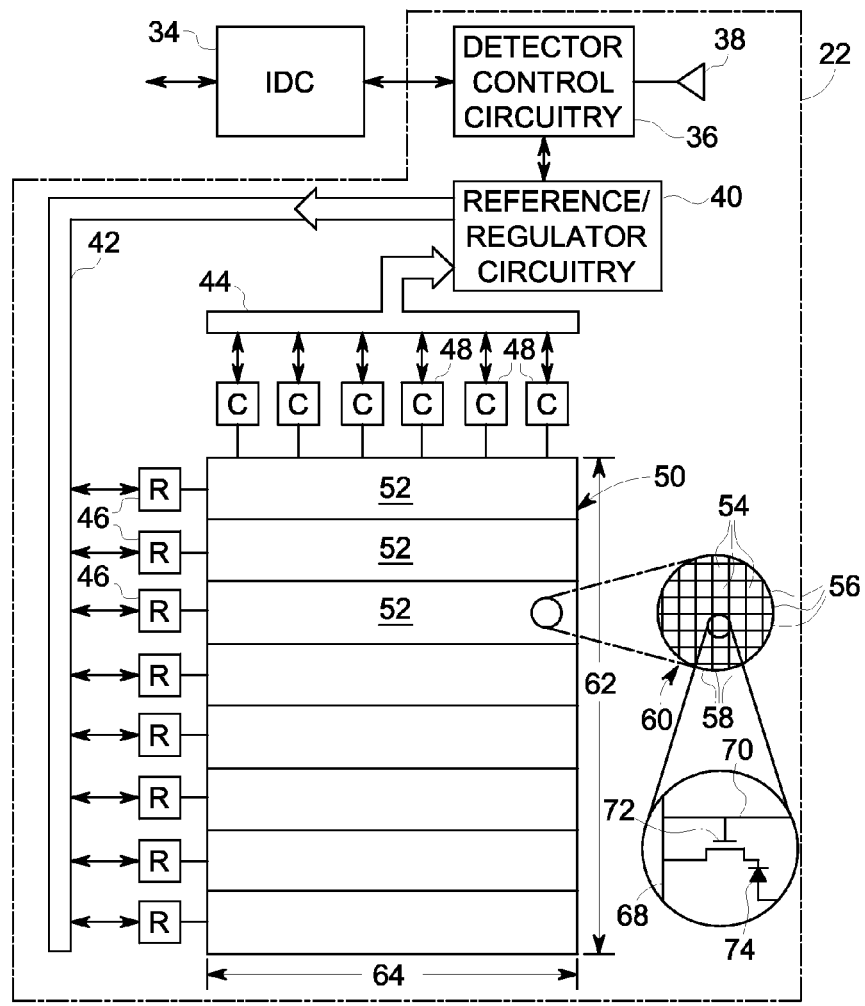
FIG. 2 is a diagrammatical representation of certain functional circuitry that may be included in a detector of the system of FIG. 1 to produce image data for reconstruction.

FIG. 2 is a diagrammatical representation of functional components of digital detector 22. FIG. 2 also represents an imaging detector controller or IDC 34, which will typically be configured within detector controller 26. IDC 34 includes a CPU or digital signal processor, as well as memory circuits for commanding acquisition of sensed signals from the detector. IDC 34 is coupled via two-way fiber optic conductors to detector control circuitry 36 within detector 22. In certain presently contemplated embodiments, other communications systems and technologies may also be used, such as Ethernet communications protocols, and wireless communications devices and protocols. IDC 34 thereby exchanges command signals for image data within the detector 22 during operation.

Detector control circuitry 36 receives DC power from a power source, represented generally at reference numeral 38. Detector control circuitry 36 is configured to originate timing and control commands for row and column electronics used to acquire image data during data acquisition phases of operation of the system. Circuitry 36 therefore transmits power and control signals to reference/regulator circuitry 40, and receives digital image pixel data from circuitry 40.

In a present embodiment, detector 22 consists of a scintillator that converts X-ray photons received on the detector surface during examinations to lower energy (light) photons. An array of photodetectors then converts the light photons to electrical signals, which are representative of the number of photons or the intensity of radiation impacting individual pixel regions of the detector surface. In certain presently contemplated embodiments, the X-ray photons may be directly converted to electrical signals. Readout electronics convert the resulting analog signals to digital values that can be processed, stored, and displayed, such as in a display 30 or a workstation 32 following reconstruction of the image. In a present form, the array of photodetectors is formed of amorphous silicon. The array elements are organized in rows and columns, with each element consisting of a photodiode and a thin film transistor. The cathode of each diode is connected to the source of the transistor, and the anodes of all diodes are connected to a negative bias voltage. The gates of the transistors in each row are connected together and the row electrodes are connected to the scanning electronics as described below. The drains of the transistors in a column are connected together and the electrode of each column is connected to an individual channel of the readout electronics.

In the particular embodiment illustrated in FIG. 2, by way of example, a row bus 42 includes a plurality of conductors for enabling readout from various rows of the detector 22, as well as for disabling rows and applying a charge compensation voltage to selected rows, where desired. A column bus 44 includes additional conductors for commanding readout from the columns while the rows are sequentially enabled. Row bus 42 is coupled to a series of row drivers 46, each of which commands enabling of a series of rows in the detector 22. Similarly, readout electronics 48 are coupled to column bus 44 for commanding readout of all columns of the detector 22.

In the illustrated embodiment, row drivers 46 and readout electronics 48 are coupled to a detector panel 50, which may be subdivided into a plurality of sections 52. Each section 52 is coupled to one of the row drivers 46, and includes a number of rows. Similarly, each column driver 48 is coupled to a series of columns. The photodiode and thin film transistor arrangement mentioned above thereby defines a series of pixels or discrete picture elements 54 which are arranged in rows 56 and columns 58. The rows and columns define an image matrix 60, having a height 62 and a width 64.

As also illustrated in FIG. 2, each pixel 54 is generally defined at a row and column crossing, at which a column electrode 68 crosses a row electrode 70. As mentioned above, a thin film transistor 72 is provided at each crossing location for each pixel, as is a photodiode 74. As row drivers 46 enable each row, signals from each photodiode 74 may be accessed via readout electronics 48, and converted to digital signals for subsequent processing and image reconstruction. Thus, an entire row of pixels in the array is controlled simultaneously when the scan line attached to the gates of all the transistors of pixels on that row is activated. Consequently, each of the pixels in that particular row is connected to a data line, through a switch, which is used by the readout electronics to restore the charge to the photodiode 74.

It should be noted that in certain systems, as each of the associated dedicated readout channels restores the charge to all the pixels in a row simultaneously, the readout electronics is converting the measurements from the previous row from an analog voltage to a digital value. Furthermore, the readout electronics may transfer the digital values from rows before the acquisition subsystem, which will perform some processing prior to displaying a diagnostic image on a monitor or writing it to film.

The circuitry used to enable the rows may be referred to in a present context as row enable or field effect transistor (FET) circuitry based upon the use of field effect transistors for such enablement (row driving). The FETs associated with the row enable circuitry described above are placed in an "on" or conducting state for enabling the rows, and are turned "off" or placed in a non-conducting state when the rows are not enabled for readout. Despite such language, it should be noted that the particular circuit components used for the row drivers and column readout electronics may vary, and the present invention is not limited to the use of FETs or any particular circuit components.

As described more fully below, it has, in general, been determined that the EMI-originating artifacts that may be present in image data can be characterized by acquiring the image data (which will include both the desired image data and the EMI noise), and processing this data to characterize the EMI noise, which may then be removed to obtain a corrected image. In a presently contemplated embodiment described below, image data is readout along with offset data, and both of these readout operations includes reading out data with the rows enabled (i.e., "FET on") and with the rows disabled (i.e., "FET off"). The overall scheme for such correction is represented diagrammatically in FIG. 3.

Figure 3:
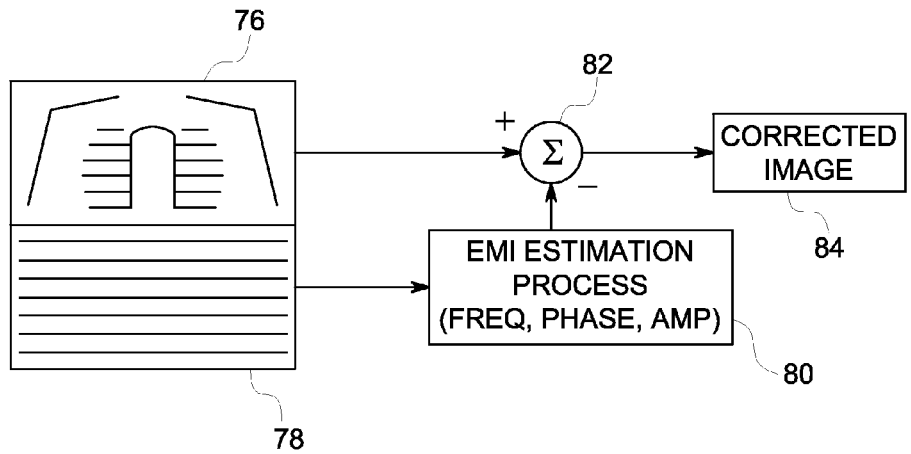
FIG. 3 is a diagrammatical overview of an exemplary presently contemplated system for eliminating EMI-originating artifacts from X-ray image data.

As shown in FIG. 3, as a first step in the process, X-ray image data is acquired as indicated by reference numeral 76. This may be done in a conventional manner using a digital detector of the type described above. Moreover, the image data is acquired with rows enabled in order to readout the depletion of charge of photodiodes in the detector caused by the attenuation, scattering or absorption of X-rays by the subject. This readout is accompanied by readout of EMI-characterizing data as represented generally by reference numeral 78. This readout is performed with the rows disabled to obtain information only on the EMI-originating noise (and any offset used in data processing). The latter dataset is then used in an EMI estimation process as indicated by reference numeral 80, in which the EMI data characterizes the interference in frequency, phase and amplitude. In a presently contemplated embodiment, because the acquisition of EMI-characterizing data follows immediately in the acquisition sequence from the image data acquisition, the phase of the EMI characterizing data is assured of being the same as the phase of the image data. Next, the characterized EMI components are subtracted from the original image data (which would otherwise include the EMI components and any artifacts they might cause), as indicated by summer 82, to arrive at corrected image data 84. It has been found that the technique allows for very accurate characterization of EMI-originating artifacts in the data, removal of these artifacts, and presentations of greatly enhanced corrected images reconstructed from the corrected data.

The particular approach to collecting data used to characterize the EMI and to correct image data to eliminate any EMI-originating artifacts is described in greater detail below. However, the approach to analysis of the EMI for purposes of characterization is presented through the following discussion. In accordance with the invention, then, this approach is employed for characterization of the EMI once the image data and EMI-characterizing data are acquired and stored as described more fully below.

The EMI can be described as a sinusoidal signal in the time domain. Because data for all pixels on each row of the image are acquired at the same time, they are affected by the EMI with the same phase. If the strength of the EMI is the same across the whole detector as is seen in most clinical images, the degree of perturbation is the same for all pixels on a row of the image.

Thus, artifacts due to EMI can be obtained by averaging pixel values on each row of the image to reduce the random additive noise introduced by the measurement system. When EMI strength varies across the detector, the averaging operation cannot be performed over the whole row. In that case, the image should be divided into ROIs (region of interest) and the averaging is then performed with each of the ROIs.

Because the EMI artifact is generally a sinusoidal signal, the contrast of the artifact in the image is determined by the amplitude of the sinusoid. The problem of estimating artifact contrast becomes the estimation of the amplitude of the sinusoid. If $f_{EMI}$ and $a_{EMI}$ are, respectively, the frequency and amplitude of the sinusoid, the artifact can be described by means of the following formula:

$$y(n) = a_{EMI} e^{j2\pi f_{EMI} n} + e(n) \quad (1);$$

where e(n) is the measurement system noise after averaging. The problem of interest is to estimate $a_{EMI}$ from measurement data sequence $\{y(0), y(1), \ldots, y(N-1)\}$ with N being the number of scan lines.

Moreover, the artifact for multiple scan lines can be represented by the variable Y, such that:

$$Y = [y(0) y(1) \ldots y(N-1)]^T \quad (2);$$

and $$\phi_{EMI} = [1\, e^{j2\pi f_{EMI}} \ldots e^{j2\pi f_{EMI}(N-1)}]^T \quad (3);$$

where $(\bullet)^T$ denotes the transpose matrix. Estimates of the values of $\{\hat{a}_{EMI}, \hat{f}_{EMI}\}$ and of $\{a_{EMI}, f_{EMI}\}$ may be obtained by minimizing the following nonlinear least squares (NLS) criterion:

$$C_1(a_{EMI}, f_{EMI}) = \|Y - a_{EMI} \phi_{EMI}\|^2 \quad (4);$$

$\|\bullet\|$ where denotes the Euclidean norm. When the noise e(n) is a zero-mean white Gaussian random process, the NLS estimates coincide with maximum likelihood (ML) estimates. When the noise is colored, however, the NLS estimates are no longer the ML estimates, but they can still have excellent statistical performance.

Minimizing the cost function $C_1$ in equation (4) with respect to $a_{EMI}$ gives the estimate of $a_{EMI}$:

$$\hat{a}_{EMI} = (\phi_{EMI}^H \phi_{EMI})^{-1} \phi_{EMI}^H Y = \phi_{EMI}^H Y / N \quad (5);$$

where $(\bullet)^H$ denotes the complex conjugate transpose.

By inserting equation (5) into equation (4):

$$\|Y - \phi_{EMI} \phi_{EMI}^H Y / N\|^2 = (Y - \phi_{EMI} \phi_{EMI}^H Y / N)^H (Y - \phi_{EMI} \phi_{EMI}^H Y / N) \quad (6)$$
$$= Y^H Y - Y^H \phi_{EMI} \phi_{EMI}^H Y / N;$$

which is minimized by maximizing:

$$C_2(f_{EMI}) = (\phi_{EMI}^H Y)^H (\phi_{EMI}^H Y) / N \quad (7).$$

Hence $f^{EMI}$ can be determined by:

$$\hat{f}_{EMI} = \underset{f_{EMI}}{\arg\max} \{|\phi_{EMI}^H Y|^2 / N\}. \quad (8)$$

Once $f^{EMI}$ is obtained, the amplitude $a^{EMI}$ is ready to be determined from equation (5):

$$\hat{a}_{EMI} = \phi_{EMI}^H Y / N |_{f_{EMI} = \hat{f}_{EMI}} \quad (9).$$

It is seen that the term:

$$\phi_{EMI}^H Y = \sum_{n=0}^{N-1} y(n) e^{-j2\pi f_{EMI} \cdot n}, \quad (10)$$

in both equations (8) and (9) is the discrete Fourier transform of sequence $[y(0), y(1), \ldots, y(N-1)]$ that can be calculated via an FFT. Hence, the amplitude of the sinusoid can be calculated from the highest peak of amplitude of the FFT divided by N.

It should be noted that the resolution of the frequency estimate from the above FFT may be limited by the number of rows, N. In some cases, this may not be considered accurate enough to correct the artifact. In that case, either the resolution may be increased by padding zeros in the sequence [y(0), y(1), ..., y(N−1), 0, ..., 0] before performing the FFT, or a refining search may be performed around the initial frequency estimate obtained from the FFT. The more accurate amplitude estimate is then updated from equation (9) with the refined frequency estimate.

It can be shown that when the EMI consists of multiple frequencies, the amplitudes can also be calculated in a similar way. When the peaks are well separated in the frequency domain, the height of each peak gives the amplitude of each of the frequencies. When two frequencies are too close to be separated in the frequency domain, the amplitude of the frequencies can be obtained iteratively by removing the obtained sinusoids from the data sequence [y(0), y(1), ..., y(N−1)].

The approach described above can obtain the best estimation of the sinusoid amplitude. It is not sensitive to electronic noise that may change, such as with panel temperature of the detector.

The foregoing estimation process may be used for the amplitude and frequency of the EMI. As discussed below, the phase of the EMI in a currently contemplated approach is not an issue because data used to characterize the EMI is inherently in phase with data collected for the X-ray image. That is, as discussed below, the EMI-characterizing data is acquired in the same data acquisition sequence or protocol but where the row enabling FETs are simply switched to an off state. Thus, when the EMI is characterized, it may be subtracted from the image data in a straightforward manner without requiring accounting for or performing phase shifts.

It should be noted that this EMI estimation approach may find application beyond the characterization and image data correction implementations described herein. For example, in the EMI monitoring system where the frequency and amplitude of the sinusoids are calculated real-time during image acquisition, warning signals are sent to the operator in the presence of the EMI. Because different observers have different visual sensitivities for artifacts with different frequencies, the warning threshold is also frequency dependent. A further application may involve the adjustment of the exposure techniques including kvp, ma, mas, filtration, and so forth according to the frequency and amplitude of the interference to reduce or eliminate the artifact in the X-ray image. Yet another application may involve warning of the operator to install shielding equipment, such as a shielding shell over the detector, once the artifact is beyond the threshold.

For a given point in space, the electromagnetic interference (EMI) can be described as a summation of K sinusoids in time domain:

$$e(t) = \sum_{k=1}^{K} a(k) \cdot e^{j2\pi \cdot f(k) \cdot t}, \quad (11)$$

where f(k) is the frequency and $$a(k) = |a(k)| e^{j \cdot \phi(k)} \quad (12)$$

is a complex number representing the amplitude |a(k)| and phase φ(k) of the kth sinusoid. From one place to the other, the frequency of the sinusoids remains the same, the amplitude and phase, however, may change depending on the orientation and distance between the source and the observation point.

The interference is added to or, more generally affects the X-ray image data through the detector panel and readout circuits described above. In particular, as discussed above, the pixels on the panel are arranged as a two-dimensional matrix with one column being read by means of a specific readout circuit via a data line. The scan lines control the order and time instant of the readout of a pixel. The pixels on a row of the panel are connected by one scan line so that each row is read out at the same time. As a result, the additive interference appears as a row correlated noise (RCN) type of artifact that is seen as lines or bands in the row direction of the image.

The additive value of the pixel located at row m and column n can be represented by:

$$\tilde{e}_{m,n} = \sum_{k=1}^{K} \tilde{a}_n(k) \cdot e^{j2\pi \cdot \tilde{f}(k) \cdot m}, \quad (13)$$

where $\tilde{f}(k)$ is the frequency of the artifact on the column direction, and $$\tilde{a}_n(k) = |\tilde{a}_n(k)| e^{j\tilde{\phi}_n(k)} \quad (14)$$

represents the amplitude $|\tilde{a}_n(k)|$ and phase $\tilde{\phi}_n(k)$ of the kth sinusoid on column n of the image. Note that the frequency of the image artifact $\tilde{f}(k)$ may be different from the EMI frequency $f(k)$ depending on the relationship between the EMI frequency and the detector line scanning frequency. For instance, if the line time of a portable detector is 0.122496 ms, this corresponds to a line scanning frequency of 1/0.122496 ms=8.164 KHz. According to the signal sampling theorem, when $f(k)$ is less than half of the line scanning frequency, that is 8.164/2=4.082 KHz, the two frequencies are equal. When $f(k)$ is higher than 4.082 KHz in this example, which is usually the case in the field, the two frequencies are different. The amplitude and phase represented by $\tilde{a}_n(k)$ is a function of the column n due to the physical location difference of the columns. The relationship between $\tilde{a}_n(k)$ and $a(k)$ depends not only on the attenuation of the detector case to the EMI, but also the impedance of the interference pickup mechanism.

The problem of interest here is to estimate the parameters of the sinusoids $\{\tilde{a}_n(k), \tilde{f}(k)\}_{k=1}^{K}$ so as to reconstruct the image artifact $\{\tilde{e}_{m,n}\}$ and then remove it from the image:

$$\hat{p}_{m,n} = p_{m,n} - \tilde{e}_{m,n} \ (m=0, 1, \ldots, M-1; n=0, 1, \ldots, N-1) \quad (15),$$

where M and N represent image size, $p_{m,n}$ is the pixel located at row m and column n of the EMI contaminated image, $\tilde{e}_{m,n}$ is the corresponding additive pixel value that is defined by equation (13), and $\hat{p}_{m,n}$ is the EMI corrected pixel value.

The parameters of the sinusoids $\{\tilde{a}_n(k), \tilde{f}(k)\}_{k=1}^{K}$ are difficult to estimate from the EMI-containing image data due to the structure that the image contains. However, it has been found that the artifact is independent of the FET state. That is, the additive noise picked up by the detector does not change, regardless of the FET state (i.e., on or off). Thus, the EMI information may be obtained by acquiring one frame of FET-off image data before the FET-on frames of any offset or light images. The present technique uses this acquisition, and the characterizing approach described above to correct the EMI-containing image data. This correction algorithm may be the first of several methods, as discussed in detail below, used by the system to reduce the effects of the EMI.

Acquisition of data from the detector with the FETs on and off permits estimation of the parameters of the artifacts that are described by the summation of K sinusoids from the "extended" rows of the image (i.e., rows of image data and rows of EMI-characterizing data). Because some of the data is acquired with the FET off in accordance with the present technique described below, the structure can be easily removed from the EMI-free offset that is obtained with the same techniques in the absence of EMI.

Thus, if $\{d_0, d_1, \ldots, d_{M-1}, d_M, \ldots, d_{M+L-1}\}$ is a vector obtained from the row extended image where $\{d_0, d_1, \ldots, d_{M-1}\}$ corresponds to the normal image and $\{d_M, \ldots, d_{M+L-1}\}$ data for rows with the FET off, the vector could be a column or the average of several columns of the image (but in a presently contemplated embodiment, is nevertheless localized to a part of the detector). If a new vector is defined by using $\{d_M, \ldots, d_{M+L-1}\}$ with the reversed order:

$$e(l) = d_{M+L-1-l}, \ l=0, 1, \ldots, L-1 \quad (16),$$

the sinusoids contained in $\{d_{M-1}, \ldots, d_1, d_0\}$ become the continuation of those in vector $\{e(l)\}_{l=0}^{L-1}$. Thus, the artifact in $\{d_{M-1}, \ldots, d_1, d_0\}$ may be reconstructed by estimating the parameters of the sinusoids from $\{e(l)\}_{l=0}^{L-1}$. Thus, the image artifact due to EMI may be removed.

To implement this technique, it is desirable that the frequency estimates be accurate. For example, assuming M=L=2048, to correct the artifact on the first row of the image, a value of $e^{j2 \times 4095 \times \pi \times \tilde{f}_k}$ is calculated. Thus, errors in the frequency estimates may be significantly amplified. The initial value of the frequency estimates can be obtained by FFT, but a refining search is desired to reach a more accurate estimate. For the present purposes, it is assumed that any of many known techniques may be used for estimating the parameters of the sinusoids.

As noted above, the correction algorithm can be implemented in the detector. It can also be implemented in the detector or system control circuitry, or even by post-processing in a remote computer. In the latter case, either entire rows with image and EMI characterization data may be transferred to the processing circuitry or the size of these combined rows may be reduced by averaging several columns and then saving the vectors in unused regions of the image. For example, a number of lines of the image (e.g., 12 lines on each of the image borders) may be used to store the averaged column vectors. In this case, the image size will be the same as before. Alternatively, the size of the image may be extended.

Moreover, the image artifact for all offset and X-ray images may be corrected. In case no EMI is present, the amplitude of the sinusoidal estimates will be equal or close to zero. Thus, when EMI is not present, the normal image acquisition and processing may be conducted. When EMI is detected, the "extended" images with row and EMI characterizing data may be acquired and EMI correction performed. Still further, the vector may be stored of the row and EMI characterizing data in the unused regions of the image and EMI correction may be performed when the observer (a physician in a medical context) sees the artifact in the image.

Moreover, an EMI-free reference FET-off image can be obtained regularly through detector quality checking or detector calibration. It can also be obtained from the image including row data and EMI characterizing data when EMI is not detected. The latest obtained EMI-free FET-off image may be used or the last several images may be averaged. In the case of using the averaged image, a simple average or weighted average may be employed, where the most recent image has the largest weight.

Figure 4:
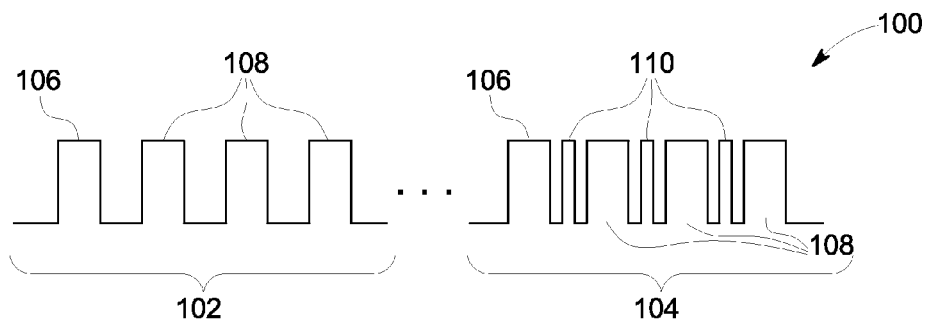
FIG. 4 is a diagrammatical representation of a portion of an acquisition sequence in which both image data, offset data and EMI characterizing data are acquired for correction of EMI data artifacts.

FIG. 4 represents an image data acquisition protocol timeline designed to permit the characterization of EMI and the correction of image data in accordance with foregoing principles of the first method. As noted above, the rows of the detector are enabled by driver circuitry, typically by altering the state of one or more FETs used in the driver circuitry. To read data from the rows, then, the FET circuitry is turned on to enable such readout. The timeline, designated generally by reference numeral 100, may include two periods of data readout 102 and 104. In an offset period 102, offset data is read out that is affected by the EMI, when such EMI is present. As discussed above, EMI-originating artifacts are independent of FET status. That is, the EMI artifact detected by the detector is the same with the FET on and the FET off. Thus, the offset period 102 includes a FET off frame 106 followed by one or more FET on frames 108. In addition, FET on frames 108 could include both normal rows with FET on and "extended" rows with FET off for continuous EMI estimate and variation tracking.

Following the offset period 102 in the data acquisition protocol, the X-ray source is activated during a reception period 104. For the reasons discussed above, the reception period 104 begins with the FET off frame 106. During the FET off frame 106, the rows are disabled. Data collected during the FET off frame 106 will be affected by the EMI present at the system, but will not include image data due to the disabling of the rows. Next, the detector is impacted by X-ray radiation during an X-ray pulse 110. During the X-ray pulse 110, the X-ray radiation will cause depletion in the charge of the photodetectors at each pixel location corresponding to the amount of X-ray radiation received at the location on the scintillator. The X-ray pulse 110 is followed by the FET on frame 108 of data readout during which the rows are enabled. As discussed below, this readout 108, in accordance with the present technique, will include readout of image data that is affected by EMI, when EMI is present at the system, as well as data used to reconstruct the useful image. That is, similar to offset 108, FET on frame 108 for x-ray image acquisition could also include both normal rows with FET on and "extended" rows with FET off for continuous EMI estimate for reconstruction. Next, one or more additional cycles of the X-ray pulse 110 followed by the FET on frame 108 may be performed to complete the fluoroscopy procedure.

The data that is collected using the first method is used to characterize the EMI such that it can be subtracted from the image data as described above. The duration of the periods for reading out image data, offset data and EMI characterizing data may vary, with these periods being equal to one another or typically with the EMI characterizing data readout being shorter. This period could be longer, however, where desired. In general, the duration during which the readout is performed will be known due to the number of rows in the detector.

Figure 5:
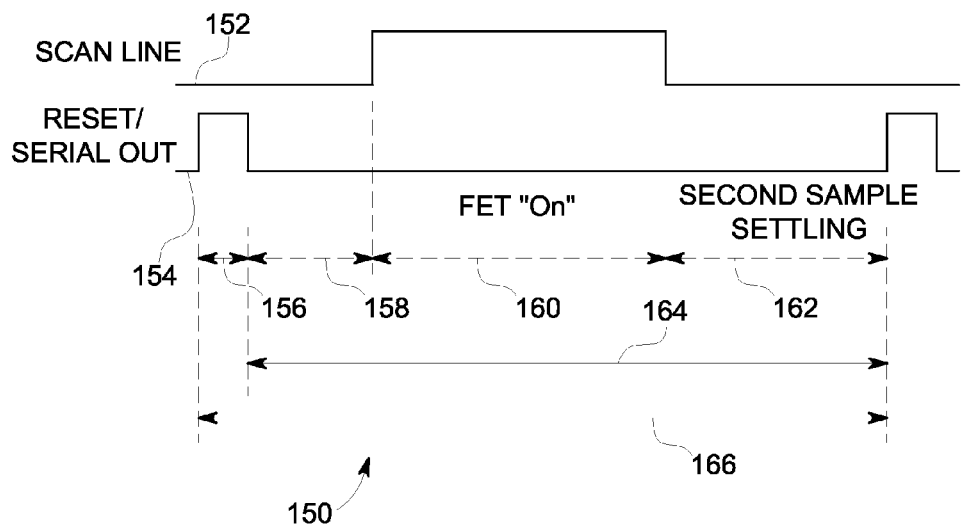
FIG. 5 is a timing drawing showing line time and integration time according to an embodiment.

FIG. 5 is a timing diagram 150 showing a scan line 152 and a reset/serial out 154. The scan line 152 indicates whether the FET is on or off. The reset/serial out 154 shows an integrator reset time 156, a first sample settling time 158, a FET on time 160, and a second sample settling time 162. An integration time 164 is the sum of the first sample setting time 158, the FET on time 160, and the second sample settling time 162. A line time 166 is the sum of the integrator reset time 156, the first sample settling time 158, the FET on time 160, and the second sample settling time 162.

In a second method to reduce the effects of the EMI, the integration time 164 may be varied while maintaining the line time 166. In a third method to reduce the effects of the EMI, the line time 166 may be varied while maintaining the integration time 164. Both of these methods are discussed in detail below. For example, the line time 166 can be varied by adjusting the FET on time 160 and/or the second sample settling time 162. The EMI noise source often occurs at frequencies that are much higher than the line read-out frequency of the imaging detector. This causes the EMI noise signal to be aliased to a lower frequency within the detector bandwidth. If the true frequency of the EMI noise signal can be determined, the line time 166 of the detector can be adjusted in such a way as to place the aliased EMI noise signal into a null for the detector.

Figure 6:
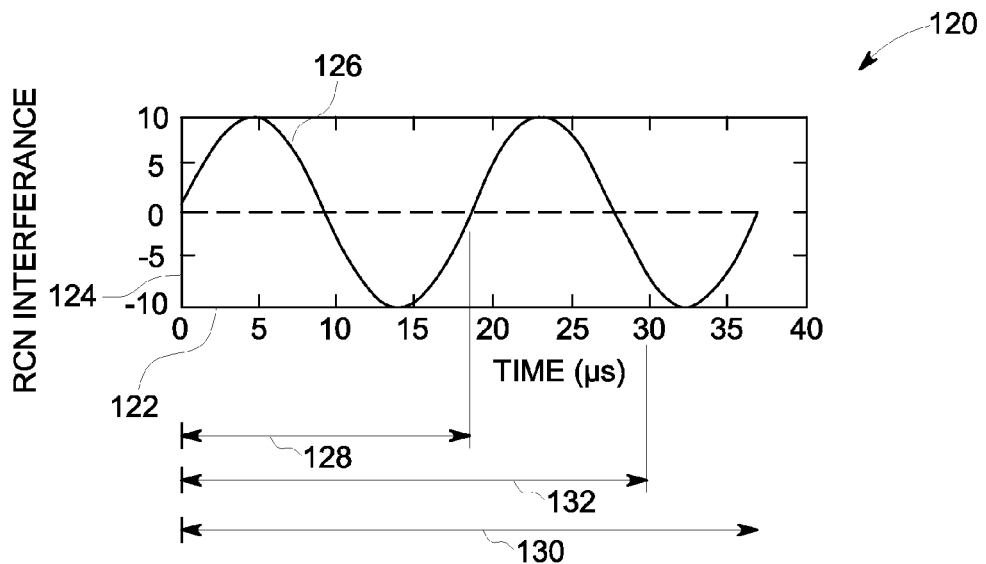
FIG. 6 is a graphical representation of an EMI-originating artifact susceptible to reduction by varying line time or integration time according to an embodiment.

To illustrate how the second and third methods may be used, FIG. 6 is a diagram 120 of the RCN as a function of time. Specifically, time in microseconds is shown on an X-axis 122 and the RCN is shown on a Y-axis 124. As shown in FIG. 6, an EMI signal 126 has a sinusoidal shape in the time domain. In addition, the EMI signal 126 has a regular period 128, which is approximately 18.5 microseconds in the illustrated embodiment. If the frequency of the EMI signal 126 is fixed or unchanging, the integration time 164 may be varied using the second method to equal the period 128 of the EMI signal 126. If the integration time 164 is the same as the period 128 of the EMI signal 126, EMI-originating artifact may be removed from the image. Using the third method, the line time 166 may be varied to equal the period 128 of the EMI signal 126. Because the integration time 164 is typically less than the line time 166, the integration time will not be the same as the period 128. Thus, the EMI-originating artifact may remain in the raw image. However, because the frequency of the EMI signal 126 is fixed, the difference between the integration time 164 and the period 128 (i.e., the residue) is constant for every scanned line such that no EMI-originating artifact will be visible in the final image. In other words, the residue between the integration time 164 and the period 128 that exists in the raw image may be removed after offset correction. The second and third methods can also be used if the integration time 164 and/or line time 166 is an integer multiple of the period 128. For example, time 130 in FIG. 6 indicates the period 128 multiplied by the integer two, which equals approximately 37 microseconds in the illustrated embodiment. If the integration time 164 is varied to equal time 130, the EMI-originating artifact may be removed from the final image. If the line time 166 is varied to equal time 130, the residue may be constant and removed after offset correction. Thus in both cases, the EMI-originating artifact is removed from the final image.

However, if the integration time 164 and/or line time 166 is not an integer multiple of the period 128, the EMI-originating artifact will remain in the final image. As shown in FIG. 6, line 132 equals approximately 30 microseconds, which is not an integral multiple of the period 128 of 18.5 microseconds. In addition, as mentioned above, both the second and third methods of varying integration time 164 and varying line time 166 assume that the frequency of the EMI signal 126 remains constant. If the frequency of the EMI signal 126 drifts with time during the fluoroscopy procedure, the RCN artifact will be visible on subsequent images. Further, both the second and third methods of varying the integration time 164 and the line time 166 are applicable to removing a single frequency artifact, or artifact with a single, base frequency and its harmonic frequencies, and may not be used when the EMI source has multiple frequencies, each of which cannot be scaled by an integer.

Figure 7:
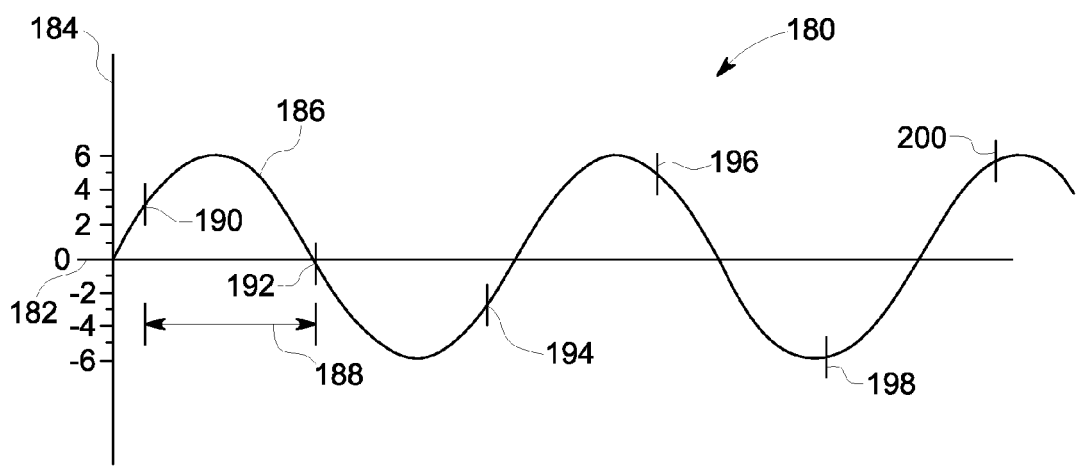
FIG. 7 is a graphical representation of an EMI-originating artifact susceptible to reduction by reordering line scans according to an embodiment.

FIG. 7 is a diagram 180 illustrating a fourth method to reduce the effects of the EMI involving reordering lines to be scanned. Specifically, the diagram 180 shows time on an X-axis 182 and the RCN on a Y-axis 184. An EMI signal 186 on an acquired image with a sinusoidal shape is shown in FIG. 7. Each of the points 190, 192, 194, 196, 198, and 200 indicate times at which image lines are obtained. Each of the points 190, 192, 194, 196, 198, and 200 may be spaced apart by a regular period 188. As shown in FIG. 7, the magnitude of the EMI signal 186 on the image may be different at each of the points 190, 192, 194, 196, 198, and 200, resulting in a RCN artifact in the final image. However, instead of scanning the images in the order of the points 190, 192, 194, 196, 198, and 200 shown in FIG. 7, the scan lines may be reordered to reduce the effect of the EMI signal 186 on the final image. Specifically, the points 190, 192, 194, 196, 198, and 200 may be reordered as shown in the following table, which also shows the value of the RCN for each of the points 190, 192, 194, 196, 198, and 200.

| Before Reordering | | After Reordering | |
| --- | --- | --- | --- |
| Line | Value | Line | Value |
| 190 | 3 | 200 | 6 |
| 192 | 0 | 196 | 5 |
| 194 | −3 | 190 | 3 |
| 196 | 5 | 192 | 0 |
| 198 | −6 | 194 | −3 |
| 200 | 6 | 198 | −6 |
| Max Δ = 12 | | Max Δ = 3 | |

In the table above, the max Δ values correspond to the maximum difference between the adjacent values of the RCN. For example, before reordering, the maximum difference between values is 12, which occurs between points 198 and 200. After reordering, the maximum difference between values is 3, which occurs between points 190 and 192, points 192 and 194, and 194 and 198. Thus, the maximum difference is reduced after reordering. Specifically, the fourth method involves reordering the line scans to reduce the line-to-line variation in the RCN. Thus, the EMI-originating artifact will vary smoothly with each scan line and may not be visible in the final image because of the low frequency of the variations between scan lines. The order of the lines may need to be selected prior to beginning the fluoroscopy procedure. Thus, implementation of the fourth method may require additional hardware in the imaging system to support reordering the scan lines before the fluoroscopy procedure. In addition, the offset data may need to be acquired in the same pattern (e.g., with the same scan line order) to avoid artifacts caused by offset mismatch. In other embodiments of the fourth method, the scan patterns may be varied to have an artifact with a very high frequency. In such cases, the artifact may be less apparent to the human eye. As with the second and third methods used to vary the integration time and line time, the fourth method of reordering the scan lines is based on an assumption of a constant frequency of the EMI source during the fluoroscopy procedure. Otherwise, the values of the RCN determined by the fourth method may not match the actual values during the fluoroscopy procedure. In addition, the fourth method may be limited to EMI sources that produce a single frequency, because it may be more difficult to generate a scanned pattern with multiple frequencies of EMI.

Figure 8:
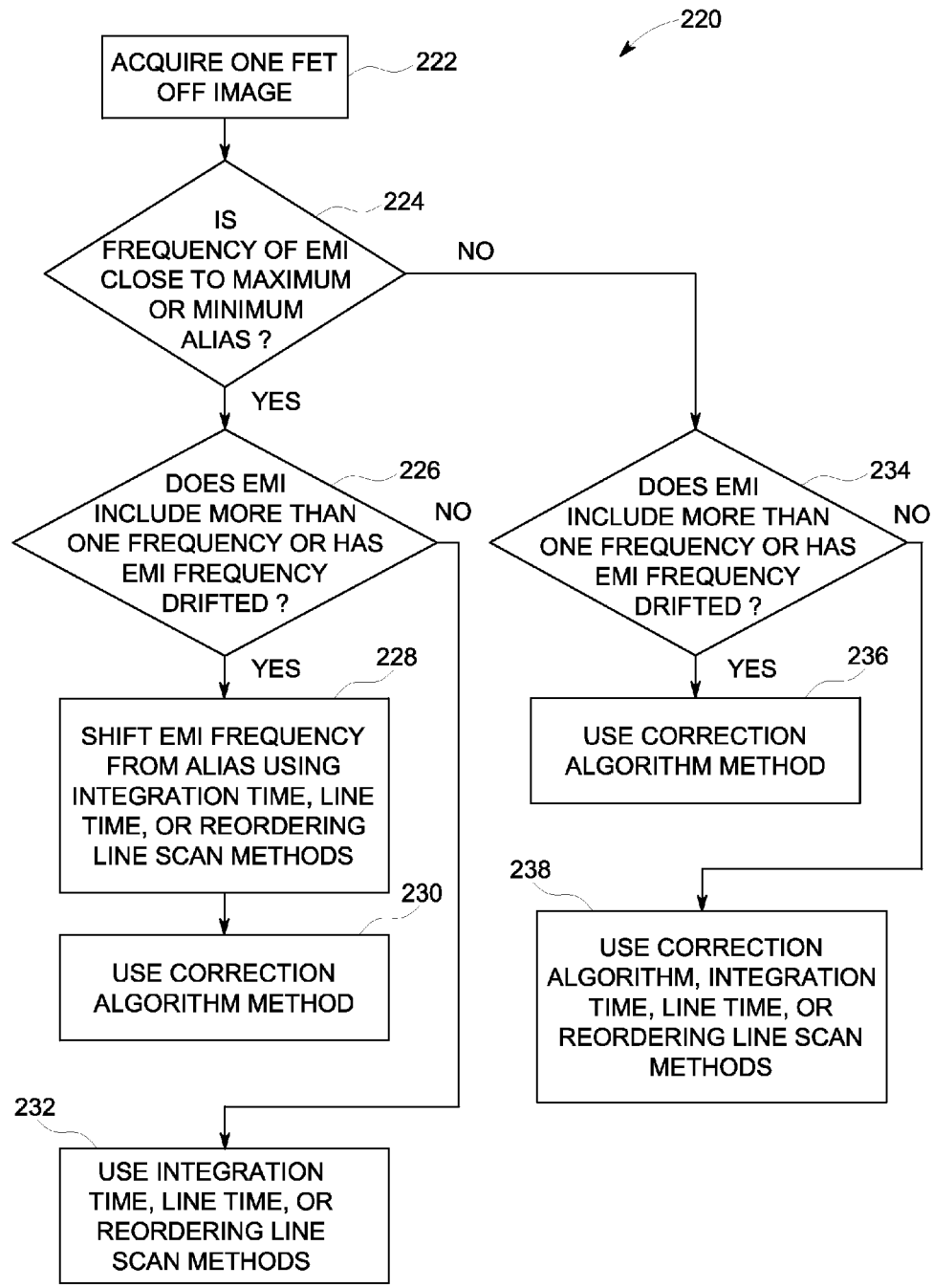
FIG. 8 is a flow diagram of a method for eliminating EMI-originating artifacts from X-ray image data.

FIG. 8 illustrates a flow chart of a method 220 that may be used to implement the first, second, third, and fourth methods discussed in detail above to reduce artifacts in X-ray image data caused by EMI sources. The method 220 takes into account advantages, disadvantages, and limitations of each of the four methods to produce an algorithm that may be used to address a variety of EMI sources. An embodiment of the invention may be embodied in the form of computer-implemented processes and apparatuses for practicing those processes. Embodiments of the present invention may also be embodied in the form of a computer program product having computer program code containing instructions embodied in tangible media, such as floppy diskettes, CD-ROMs, hard drives, USB (universal serial bus) drives, or any other computer readable storage medium, wherein, when the computer program code is loaded into and executed by a computer, the computer becomes an apparatus for practicing embodiments of the invention. Embodiments of the invention also may be embodied in the form of computer program code, for example, whether stored in a storage medium, loaded into and/or executed by a computer, or transmitted over some transmission medium, such as over electrical wiring or cabling, through fiber optics, or via wireless transmission, wherein when the computer program code is loaded into and executed by a computer, the computer becomes an apparatus for practicing embodiments of the invention. When implemented on a general-purpose processor, the computer program code segments configure the processor to create specific logic circuits. A technical effect of the method 220 may include, among others, characterizing EMI, selecting an EMI compensation algorithm based upon the characterized EMI, and acquiring data from a digital image detector based upon the selected EMI compensation algorithm. In certain embodiments, the EMI compensation algorithm is selected automatically without human intervention.

Specifically, the method 220 includes obtaining a single FET-off image (block 222). This may correspond to the FET off frame 106 discussed above with respect to the first method. As discussed above, the FET-off image may include the RCN. Next, the system 10 determines the frequency of the EMI and compares the frequency with maximum and minimum alias frequencies (block 224) to determine whether the first method may be appropriate. The first method may fail to remove EMI-originating artifacts at maximum or minimum alias frequencies because of the limited number of row data and phase shifts with time. If the frequency of the EMI is close to the maximum or minimum alias values, the system 10 determines whether the EMI includes more than one frequency or if the frequency of the EMI has drifted with time (block 226). As discussed above, the second, third, and fourth methods may not be appropriate when the EMI includes more than one frequency or the EMI frequency has drifted. Thus, if the EMI includes more than one frequency or the frequency of the EMI has drifted, the system 10 may shift the EMI frequency away from the maximum or minimum alias values using one or more of the second method (varying integration time), third method (varying line time), or fourth method (reordering line scan) discussed above (block 228). Once the effect of the maximum or minimum alias values has been removed by the system 10, the first method may be used to remove the EMI-originating artifact from the final image (block 230). If the EMI does not include more than one frequency, or the EMI frequency has not drifted, then one or more of the second, third, or fourth methods may be used (block 232) without subsequent use of the first method.

If the frequency of the EMI is not close to the maximum or minimum alias values, the system 10 determines whether the EMI includes more than one frequency or whether the frequency of the EMI has drifted (block 234). If the EMI includes more than one frequency or the frequency of the EMI has drifted, the system 10 uses the first method to remove EMI-originating artifacts because the second, third, and fourth methods may not be appropriate (block 236). If the EMI does not include more than one frequency or the EMI frequency has not drifted, the system 10 may use one or more of the first, second, third, or fourth methods discussed above (block 238). Thus, depending on the characteristics of the EMI signal, the system 10 selects one or more of the methods discussed above to be used sequentially or in combination with one another to reduce the EMI-originating artifacts from the final image. For example, the system may determine at least two frequencies and/or phases of the EMI and select at least two methods for each of the at least two frequencies and/or phases of the EMI. In addition, the methods discussed above may be divided into those that direct an alteration in a manner in which imaging data is acquired (e.g., the second, third, and fourth methods) and those that are performed on the imaging data after acquisition (e.g., the first method).

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for controlling a X-ray radiography system, comprising:
acquiring data from a digital X-ray detector;
characterizing electromagnetic interference based upon the acquired data;
selecting an electromagnetic interference compensation algorithm based upon the characterized electromagnetic interference;
acquiring X-ray imaging data via the digital X-ray detector based upon the selected electromagnetic interference compensation algorithm; and
processing the X-ray imaging data to produce image data capable of reconstruction in a user viewable form;
wherein the electromagnetic interference compensation algorithm is selected automatically without human intervention.

2. The method of claim 1, comprising selecting more than one electromagnetic interference compensation algorithm to be used together to reduce effects of the characterized electromagnetic interference on the imaging data.

3. The method of claim 2, comprising determining at least two frequencies and/or phases of the electromagnetic interference, and selecting at least two electromagnetic interference compensation algorithms for each of the at least two frequencies and/or phases.

4. The method of claim 2, wherein the electromagnetic interference compensation algorithms comprise at least one algorithm directing alteration in a manner in which the imaging data is acquired.

5. The method of claim 4, wherein the at least one algorithm directs acquisition of the imaging data in phase with the characterized electromagnetic interference.

6. The method of claim 4, wherein the at least one algorithm directs acquisition of the imaging data for lines of the digital X-ray detector that begin at substantially the same phase of the characterized electromagnetic interference.

7. The method of claim 4, wherein the at least one algorithm directs acquisition of lines of imaging data from the digital X-ray detector in an order that is based upon the frequency of the characterized electromagnetic interference.

8. The method of claim 4, wherein two different electromagnetic interference compensation algorithms are selected, including a first algorithm directing alteration in a manner in which the imaging data is acquired, and a second algorithm that is performed on the imaging data after acquisition.

9. The method of claim 4, comprising adjusting an integration time of the digital X-ray detector based on a period of the characterized electromagnetic interference, wherein adjusting comprises setting the integration time as close as possible to an integer multiple of the period of the characterized electromagnetic interference.

10. The method of claim 4, wherein the at least one algorithm determines a plurality of values of the characterized electromagnetic interference using a first scan line order and sorts the plurality of values of the characterized electromagnetic interference to obtain a second scan line order, wherein a visibility of the characterized electromagnetic interference is reduced in image data obtained using the second scan line order.

11. The method of claim 2, wherein the electromagnetic interference compensation algorithms comprise at least one algorithm that is performed on the imaging data after acquisition.

12. The method of claim 11, comprising performing a series of imaging data acquisitions in a fluoroscopy mode of operation, and acquiring data for characterizing the electromagnetic interference between successive acquisitions of imaging data.

13. An imaging system comprising:
an X-ray source,
a digital X-ray detector;
control circuitry configured to acquire data via the digital X-ray detector including X-ray image data and data resulting from electromagnetic interference, characterize the electromagnetic interference based upon the acquired data, select an electromagnetic interference compensation algorithm based upon the characterized electromagnetic interference, and acquire X-ray imaging data via the digital X-ray detector based upon the selected electromagnetic interference compensation algorithm; and
processing circuitry configured to process the X-ray imaging data to produce image data capable of reconstruction in a user viewable form;
wherein the electromagnetic interference compensation algorithm is selected automatically without human intervention.

14. The imaging system of claim 13, wherein the control circuitry is configured to select more than one electromagnetic interference compensation algorithm to be used together to reduce effects of the characterized electromagnetic interference on the imaging data.

15. The imaging system of claim 14, wherein the electromagnetic interference compensation algorithms comprise at least one algorithm directing alteration in a manner in which the imaging data is acquired.

16. The imaging system of claim 15, wherein the at least one algorithm directs acquisition of lines of imaging data from the digital X-ray detector in an order that is based upon the frequency of the characterized electromagnetic interference.

17. The imaging system of claim 14, wherein the electromagnetic interference compensation algorithms comprise at least one algorithm that is performed on the imaging data after acquisition.

18. An article of manufacture comprising:
a non-transitory computer-readable storage medium having executable application instructions stored thereon, wherein the application instructions include:
instructions adapted to receive first data from a digital image detector;
instructions adapted to characterize electromagnetic interference based upon the received data;

instructions adapted to select an electromagnetic interference compensation algorithm based upon the characterized electromagnetic interference;

instructions adapted to acquire second data from the digital image detector based upon the selected electromagnetic interference compensation algorithm; and instructions adapted to process the second data to produce image data capable of reconstruction in a user viewable form;

wherein the electromagnetic interference compensation algorithm is selected automatically without human intervention.

19. The article of manufacture of claim 18, comprising instructions adapted to select more than one electromagnetic interference compensation algorithm to be used together to reduce effects of the characterized electromagnetic interference on the first data.

20. The article of manufacture of claim 19, wherein the electromagnetic interference compensation algorithms comprise at least one algorithm directing alteration in a manner in which the first data is acquired.

21. The article of manufacture of claim 19, wherein the electromagnetic interference compensation algorithms comprise at least one algorithm that is performed on the first data after acquisition.

22. A method for dynamically selecting digital X-ray detector integration time, the method comprising:

determining a period of an electromagnetic interference signal generated by a source external to the digital X-ray detector;

adjusting an integration time of the digital X-ray detector based on the period of the electromagnetic interference signal, wherein adjusting comprises setting the integration time as close as possible to an integer multiple of the period of the electromagnetic interference signal; and selecting an electromagnetic interference compensation algorithm for reduction of electromagnetic interference automatically without human intervention.

23. A method for dynamically selecting digital X-ray detector scan line order, the method comprising:

determining a plurality of values of an electromagnetic interference signal generated by a source external to the digital X-ray detector using a first scan line order;

sorting the plurality of values of the electromagnetic interference signal to obtain a second scan line order, wherein a visibility of the electromagnetic interference signal is reduced in a digital X-ray image obtained using the second scan line order; and selecting an electromagnetic interference compensation algorithm for reduction of electromagnetic interference automatically without human intervention.

* * * * *